United States Patent [19]

Tsunakawa et al.

[11] Patent Number: 4,683,230

[45] Date of Patent: Jul. 28, 1987

[54] BMY-28121, A NEW ANTITUMOR ANTIBIOTIC

[75] Inventors: Mitsuaki Tsunakawa, Tokyo; Masataka Konishi, Kawasaki; Takeo Miyaki, Yokohama, all of Japan

[73] Assignee: Bristol-Myers Company, New York, N.Y.

[21] Appl. No.: 704,973

[22] Filed: Feb. 25, 1985

[51] Int. Cl.$^4$ ............... A61K 31/55; C07D 487/04
[52] U.S. Cl. ................... 314/214; 540/496; 435/119
[58] Field of Search ............. 540/496; 514/214

[56] References Cited

PUBLICATIONS

J. Am. Chem. Soc. 87: 5791–5793, (1965).
J. Antibiotics, 33(6): 665–667, (1980).
J. Antibiotics 27(11): 886–873 (1974).
J. Antibiotics 25(11): 668–673 (1972).
J. Antibiotics 25: 437–444 (1972).
J. Antibiotics 29(1): 93–96 (1976).
J. Antibiotics 30: 340–343 (1977).
J. Antibiotics 37: 191–199 (1984).

Primary Examiner—Robert T. Bond
Attorney, Agent, or Firm—David M. Morse

[57] ABSTRACT

A new antitumor antibiotic designated herein as BMY-28121 is produced by fermentation of *Streptomyces albus* strain K731-113 (ATCC 39897). BMY-28121, which may be recovered from the fermentation broth in either its natural free hydroxy form (BMY-28121A) or methyl ether form (BMY-28121B), inhibits gram-positive bacteria and anaerobes and inhibits the growth of mammalian tumors such as P-388 leukemia, L-1210 leukemia and B16 melanoma.

10 Claims, 4 Drawing Figures

1H NMR SPECTRUM OF BMY-28121A

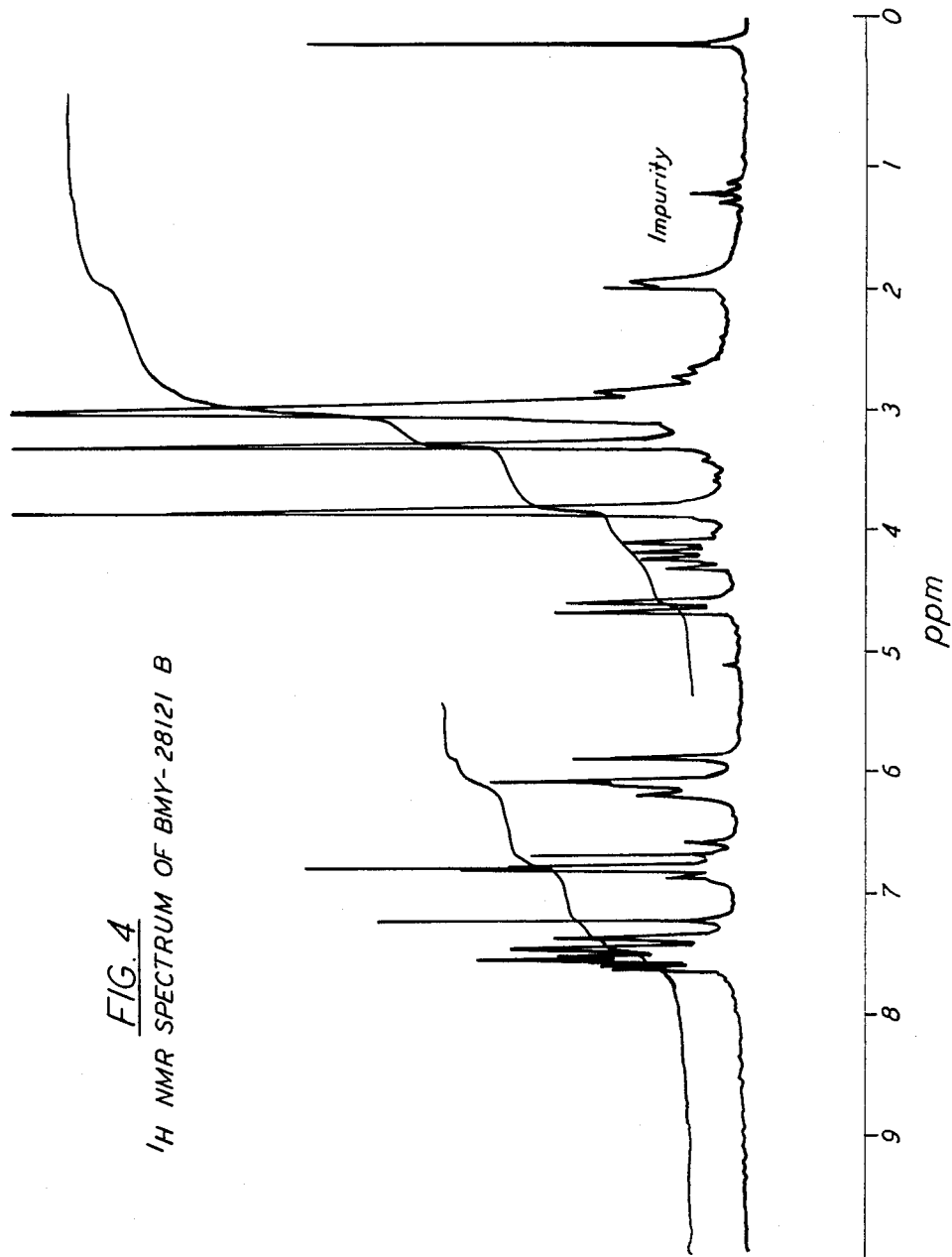

BMY-28121, A NEW ANTITUMOR ANTIBIOTIC

BACKGROUND OF THE INVENTION (1) Field of the Invention

This invention relates to novel antibiotics of the pyrrolo(1,4)benzodiazepine family having both antibacterial and antitumor activity and to their production by fermentation of a new microorganism.

(2) Description of the Prior Art

The antitumor antibiotics of the present invention are new members of the anthramycin-sibiromycin group of antibiotics.

Among the members of this group are anthramycin having the formula

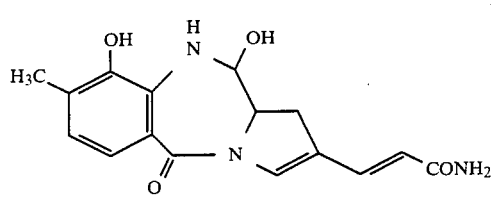

which is disclosed in *J. Am. Chem. Soc.* 87: 5791–5793, (1965), mazethramycin having the formula

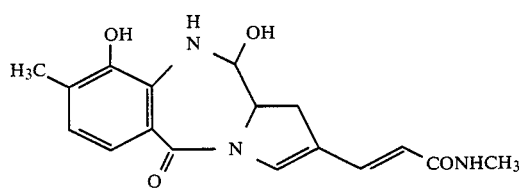

which is disclosed in *J. Antibiotics* 33(6): 665–667, (1980), sibiromycin of the formula

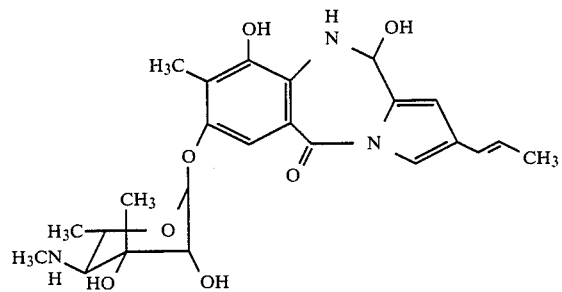

which is disclosed in *J. Antibiotics* 27(11): 866–873 (1974), and *J. Antibiotics* 25(11): 668–673 (1972), tomaymycin of the formula

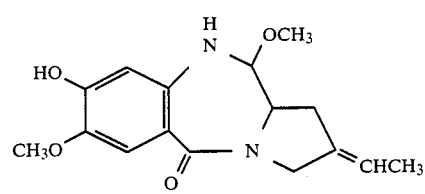

which is disclosed in *J. Antibiotics* 25: 437–444 (1972), neothramycins A and B of the formula

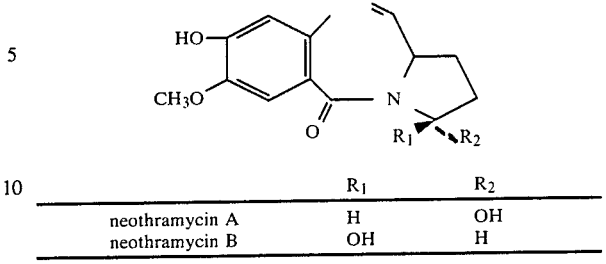

|  | $R_1$ | $R_2$ |
|---|---|---|
| neothramycin A | H | OH |
| neothramycin B | OH | H | which are disclosed in *J. Antibiotics* 29(1): 93–96 (1976) and *J. Antibiotics* 30: 340–343 (1977), and chicamycin of the formula

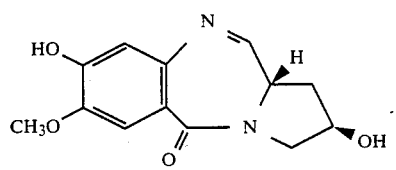

which is disclosed in *J. Antibiotics* 37: 191–199 (1984). BMY-28121 is the first example of this group which has only one substituent (9-methoxy) on the benzene ring. The absence of a hydroxy group on the ring is another unique structural characteristic of the antibiotic.

SUMMARY OF THE INVENTION

There is provided by the present invention a new pyrrolobenzodiazepine antibiotic designated herein as BMY-28121, said antibiotic being prepared by cultivating a new strain of Streptomyces designated *Streptomyces albus* strain No. K731-113 (ATCC 39897) in an aqueous nutrient medium containing assimilable sources of carbon and nitrogen under submerged aerobic conditions until a substantial amount of BMY-28121 is produced by said organism in said culture medium and then recovering the BMY-28121 antibiotic from the culture medium.

The new BMY-28121 antibiotic of the present invention may be recovered from the fermentation broth either as a methyl ether form of the structure

BMY-28121B

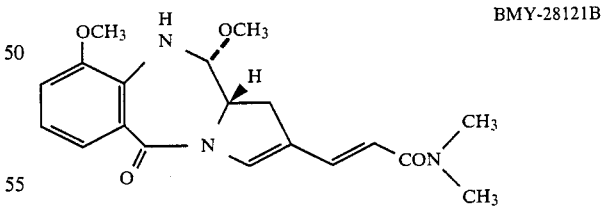

or as the natural free hydroxy form of the structure

BMY-28121A depending on the isolation procedure used. As used herein and in the claims, the term "BMY-28121" refers to the BMY-28121 antibiotic in either the methyl ether or free hydroxy form.

The BMY-28121 antibiotics of the present invention inhibit the activity of various gram-positive bacteria and anaerobes. In addition they inhibit the growth of mammalian tumors such as P388 leukemia in mice. The new antibiotics, therefore, may be used as antibacterial agents or as antitumor agents for inhibiting mammalian tumors.

DESCRIPTION OF THE DRAWINGS

FIG. 4 shows the $^1$H NMR spectrum of BMY-28121B

DETAILED DESCRIPTION

Figure 1:
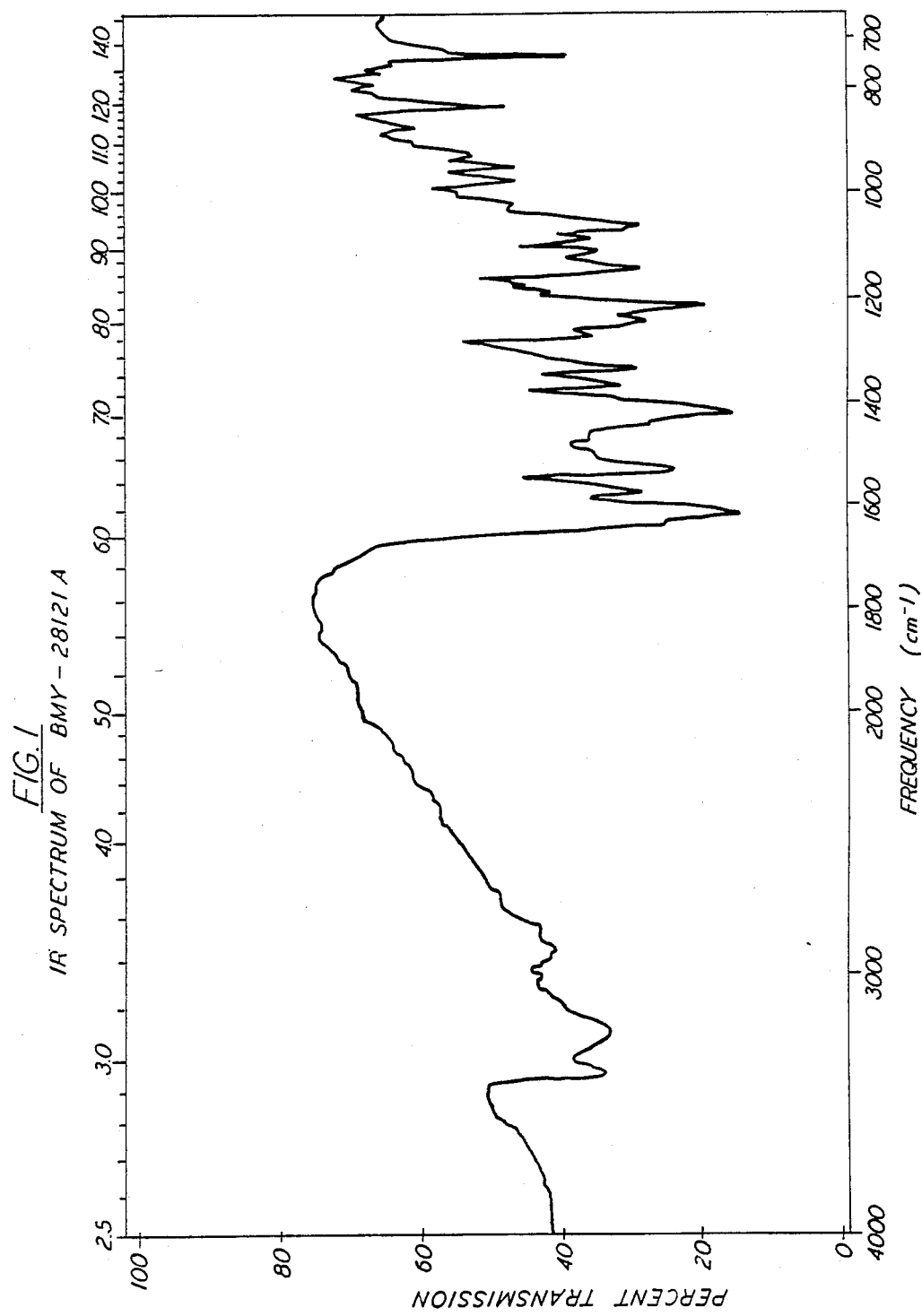
FIG. 1 shows the infrared absorption spectrum of BMY-28121A (KBr pellet)

This invention relates to novel antitumor antibiotics designated herein as BMY-28121 A and B and to their preparation by fermentation of a new strain of Streptomyces designated *Streptomyces albus* strain K731-113. The above-mentioned producing organism was isolated from a soil sample collected in Poros Island, Greece. A biologically pure culture of the organism has been deposited with the American Type Culture Collection, Washington D.C., and added to its permanent collection of microorganisms as ATCC 39897.

The Microorganism

The producing strain K731-113 was isolated from a soil sample and prepared by conventional procedures as a biologically pure culture for characterization. Results of taxonomic studies indicated that the strain belonged to the genus Streptomyces and the species *albus*.

Materials and methods

For the morphological, cultural and physiological studies, the descriptions of International Streptomyces Projects (E. B. Shirling & D. Gottlieb: *Intl. J. Syst. Bacteriol.* 16 313-340, 1966) were referred. In addition to the above methods, several other media which are recommended by S. A. Waksman (The Actinomycetes Vol. 2, 1961) were also used. Strain K731-113 was compared with the species of Streptomyces, described in *Intl. J. Syst. Bacteriol.* and *J. Antibiotics*.

Morphology

Strain K731-113 forms substrate and aerial mycelia (0.5 μm in width), both of which are long, well branched and not fragmented into rods or cocci. Chains of arthrospores are born on the aerial hyphae. The spore-chain morphology is as follows: (1) long chains, containing 10 to 50 spores, (2) flexious or open spiral on Czapek's sucrose-nitrate agar, and closed spiral with 4 to 10 turns in Bennett's agar, (3) monopodially branching sporophore. The spores are oval, 0.5−0.6×0.7−1.0 μm in size, and have smooth surface.

Sporangia, motile spores, sclerotia and verticils are not observed.

Cultural characteristics

Strain K731-113 grows moderately on most of the descriptive agar media. The aerial mycelium is formed abundantly on Czapek's sucrose-nitrate agar, ISP Nos. 2 and 4 Media and Bennett's agar, poorly or rudimentally on glucose-asparagine agar, ISP Nos. 3, 5, 6 and 7 Media, and nutrient agar. The color of aerial mycelium is white. The reverse color shows pinkish or reddish shade in ISP No. 5 Medium, and dark grayish brown in ISP No. 7 Medium. These reverse colors are, however, considered to be negligible in chromogenicity. Melanoid and other diffusible pigment are not observed in any agar media. The cultural characteristics are shown in Table 1.

Physiological characteristics

Strain K731-113 grows optimally at 28° C. The growth ranges from 15° C. to 48° C. No growth is observed at 7° C. and 50° C. Based on the methods by Mikami et al. (*Intl. J. Syst. Bacteriol.* 27 290, 1977), the tyrosinase reaction is negative. The strain hydrolyzes gelatin and starch, but not skim-milk. The NaCl tolerance for growth is seen at 15%. Among eleven diagnostic sugars described in Bergey's Manual, 8th ed. (1974), only raffinose is not utilized by the strain.

The physiological characteristics and the carbohydrate utilization are shown in Tables 2 and 3, respectively.

Cell-wall composition

According to the rapid analysis for diaminopimelic acid isomers and whole cell sugars by T. Hasegawa et al. (*J. Gen. Appl. Microbiol.* 29 319, 1983), strain K731-113 has LL-diaminopimelic acid but not any diagnostic sugars. These results indicate that the cell-wall composition belongs to Type I.

Taxonomic Position

The morphological, cultural and physiological characteristics of strain K731-113 as well as its amino acid and sugar compositions of whole cell hydrolyzate indicate that the strain is a species of the genus Streptomyces. According to the descriptions of Pridham and Tresner in Bergey's Manual, 8th ed. (1974), strain K731-113 is classified into the following species group: section Spirales (S), white series (W), non-chromogenic (C-) and smooth spore surface (SM). According to the descriptions of International Streptomyces Projects (ISP), strain K731-113 is differentiated from all 21 strains (17 species) in this species group, but is similar to *Streptomyces albus* strain No. J576-99 (ATCC 39143) (*J. Antibiotics* 37: 191–199, 1984) in the lack of ability to form distinct non-melanoid pigment, the ability to hydrolyze gelatin or starch but not casein, the high NaCl tolerance for growth and the profile of carbohydrate utilization. Strain K731-113 was therefore determined to be a strain of *S. albus*, and the culture has been deposited in the American Type Culture Collection with the accession number ATCC 39897.

TABLE 1

| Cultural characteristics of strain K731-113 | |
|---|---|
| Tryptone-yeast extract broth (ISP No. 1) | G: moderate; floccose and sedimented |
| | D: none |
| Sucrose-nitrate agar (Czapek's agar) | G: abundant |
| | R: pale yellow (89)-light yellowish brown (76) |
| | A: moderate; white |
| | D: none |
| Glucose-asparagine agar | G: poor |
| | R: yellow white (92) |
| | A: none |
| | D: none |
| Glycerol-asparagine agar (ISP No. 5) | G: moderate |
| | R: moderate yellowish pink (29)-deep reddish brown (41) |
| | A: scant to moderate; white |
| | D: light brown (57) |

TABLE 1-continued

Cultural characteristics of strain K731-113

| | | |
|---|---|---|
| Inorganic salts-starch agar (ISP No. 4) | G: | abundant |
| | R: | grayish yellow (90)-moderate olive brown (95) |
| | A: | abundant; white |
| | D: | none |
| Tyrosine agar (ISP No. 7) | G: | moderate |
| | R: | moderate yellow pink (29)-grayish brown (61) |
| | A: | scant; white |
| | D: | light brown (57) |
| Nutrient agar | G: | poor |
| | R: | light yellowish brown (76) |
| | A: | moderate; white |
| | D: | none |
| Yeast extract-malt extract agar (ISP No. 2) | G: | abundant |
| | R: | strong yellowish brown (74) |
| | A: | moderate; white |
| | D: | light yellowish brown (75) |
| Oat meal agar (ISP No. 3) | G: | moderate |
| | R: | yellowish white (92) |
| | A: | scant; white |
| | D: | none |
| Bennett's agar | G: | moderate |
| | R: | deep yellow (85) |
| | A: | moderate; white |
| | D: | none |
| Peptone-yeast extract-iron agar (ISP No. 6) | G: | moderate |
| | R: | dark orange yellow (72) |
| | A: | rudimental; white |
| | D: | pale yellow (89) |

*Observed after incubation at 28° C. for 3 weeks.
**Abbreviation: G - Growth; R - Reverse color; A - Aerial mycelium; D - Diffusible pigment
***Color and number in parenthesis follow the color standard in "Kelly, K. L. & D. B. Judd: ISCC-NBS color-name charts illustrated with Centroid Colors. US Dept. of Comm. Cir. 553, Washington, D.C., Nov., 1975"

TABLE 2

Physiological characteristics of strain K731-113

| Test | Response | Method or medium |
|---|---|---|
| Growth temperature | Maximal growth at 28° C. Growth range from 15° C. to 48° C. No growth at 7° C. and 50° C. | Bennett's agar |
| Gelatin liquefaction | Liquefied (after 4 weeks) | 1% malt extract, 0.4% yeast extract, 0.4% glucose and 20% gelatin |
| Starch hydrolysis | Hydrolyzed | Starch agar plate |
| Reaction in skim milk | Not coagulated and not liquefied | Difco skim-milk |
| Formation of melanoid pigment | Negative | ISP Nos. 1, 6 and 7 media |
| Tyrosinase reaction | Negative | Method by Mikami et al. |
| Nitrate reduction | Negative | Czapek's sucrose nitrate broth and yeast extract nitrate broth (0.5% yeast extract, 1% glucose, 0.5% KNO₃, 0.1% CaCO₃) |
| pH tolerance | Growth in pH 4.5-10.0. No growth at pH 4.0. | ISP No. 2 Medium |
| NaCl tolerance | Growth at 15% or less. | ISP No. 2 Medium |
| Lysozyme tolerance | Tolerant. Growth at 0.01% | Trypticase soy broth plus 1.5% agar |

TABLE 3

Carbohydrate utilization of strain K731-113

| | | | |
|---|---|---|---|
| Glycerol | + | Cellobiose | + |
| D(−)-Arabinose | + | Melibiose | − |
| L(+)-Arabinose | + | Trehalose | + |
| D-Xylose | + | Raffinose | − |
| D-Ribose | + | D(+)-Melezitose | + |
| L-Rhamnose | + | Soluble starch | + |
| D-Glucose | + | Cellulose | − |
| D-Galactose | + | Dulcitol | − |
| D-Fructose | + | Inositol | + |
| D-Mannose | + | D-Mannitol | + |
| L(−)-Sorbose | − | D-Sorbitol | + |
| Sucrose | + | Salicin | + |
| Lactose | + | Chitin | − |
| | | Keratin | + |

Observation after incubation at 28° C. for 2 weeks.
Basal medium: Pridham-Gottlieb's inorganic medium
Abbreviation
+: positive utilization
−: negative utilization It is to be understood that for the production of the BMY-28121 antibiotics, the present invention, though described in detail with reference to the particular strain *Streptomyces albus* strain K731-113 (ATCC 39897), is not limited to this microorganism or to microorganisms fully described by the cultural characteristics disclosed herein. It is specifically intended that the invention embraces strain K731-113 and all natural and artificial BMY-28121-producing variants and mutants thereof.

Antibiotic Production

The BMY-28121 antibiotics of the present invention may be prepared by cultivating a BMY-28121-producing strain of *Streptomyces albus*, preferably a strain of *Streptomyces albus* having the identifying characteristics of ATCC 39897 or a variant or mutant thereof, in a conventional aqueous nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate assimilable carbon source such as glycerol, arabinose, xylose, ribose, glucose, fructose, sucrose, lactose, soluble starch, mannitol or sorbitol. As nitrogen sources, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron, and the like.

Production of the BMY-28121 antibiotics can be effected at any temperature conducive to satisfactory growth of the producing organism, i.e. 15° C. to 48° C., and is conveniently carried out at a temperature of around 27°-32° C. Ordinarily, optimum production is obtained in shaker flasks after incubation periods of about 7-8 days. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium. Antibiotic production may be monitored by the paper disc-agar diffusion assay using *Bacillus subtilis* M45 (Rec⁻mutant) and *Bacteroides fragilis* as the test organism.

Isolation and Purification

The BMY-28121 antibiotic of the present invention may be obtained from the fermentation broth in two different forms, A and B, according to the procedures used for the extraction and purification of the antibiotic. Structural studies have revealed that BMY-28121B is the methyl ether form of BMY-28121A. Therefore, the antibiotic may be recovered in the natural free hydroxy form (BMY-28121A) by avoiding use of methanol in the extraction and chromatographic purification procedure, while the methyl ether form (BMY-28121B) is obtained by following the same general extraction and purification procedure, but using methanol as an extraction solvent and eluant.

Isolation of BMY-28121A: Illustrative Procedure

When fermentation is complete, the harvested broth is separated into mycelial cake and broth supernatant, for example, by using filtration or centrifugation. The mycelial cake is stirred with acetone to extract the antibiotic activity and the acetone extract then combined with the broth filtrate. The combined solution is then stirred with a nonionic, macroreticular polymer resin such as DIAION HP-20 and the resin eluted with aqueous acetone. The eluates are concentrated in vacuo to an aqueous solution which is extracted with n-butanol. Evaporation of the n-butanol extract affords crude BMY-28121A.

Purification of the crude BMY-28121A may be carried out by dissolving the crude solid in aqueous acetone and applying the solution to a column of a nonionic, macroreticular polymer resin such as DIAION HP-20 equilibrated with aqueous acetone. Elution is carried out with aqueous acetone with the eluate being monitored by bioassay against *B. subtilis* M45 (Rec⁻ mutant). Active fractions are pooled, evaporated in vacuo and lyophilized to give a semi-pure BMY-28121A. Further purification may be achieved by chromatography on silica gel developing with a chloroform-acetone mixture.

Isolation of BMY-28121 B: Illustrative Procedure

When fermentation is complete, the harvested broth is separated into mycelial cake and broth supernatant, for example by using filtration or centrifugation. The mycelial cake is stirred with methanol to extract the antibiotic activity. The broth supernatant is stirred with a nonionic, macroreticular polymer resin such as DIAION HP-20 and the resin eluted with aqueous acetone. The acetone and methanol extracts are combined and concentrated in vacuo to an aqueous solution which is extracted with n-butanol. Evaporation of the butanol extracts affords crude BMY-28121B.

Purification of the crude BMY-28121B may be carried out by dissolving the crude solid in aqueous methanol, applying the solution to a column of a nonionic, macroreticular polymer resin such as DIAION HP-20 and developing with aqueous methanol. The eluate is monitored by assay against *B. subtilis* M45. The appropriate eluates are pooled and concentrated in vacuo to give semi-pure BMY-28121B. This solid may be further purified by chromatography on a silica gel column using a mixture of chloroform-methanol as the developing solvent.

Physico-chemical Properties

Figure 2:
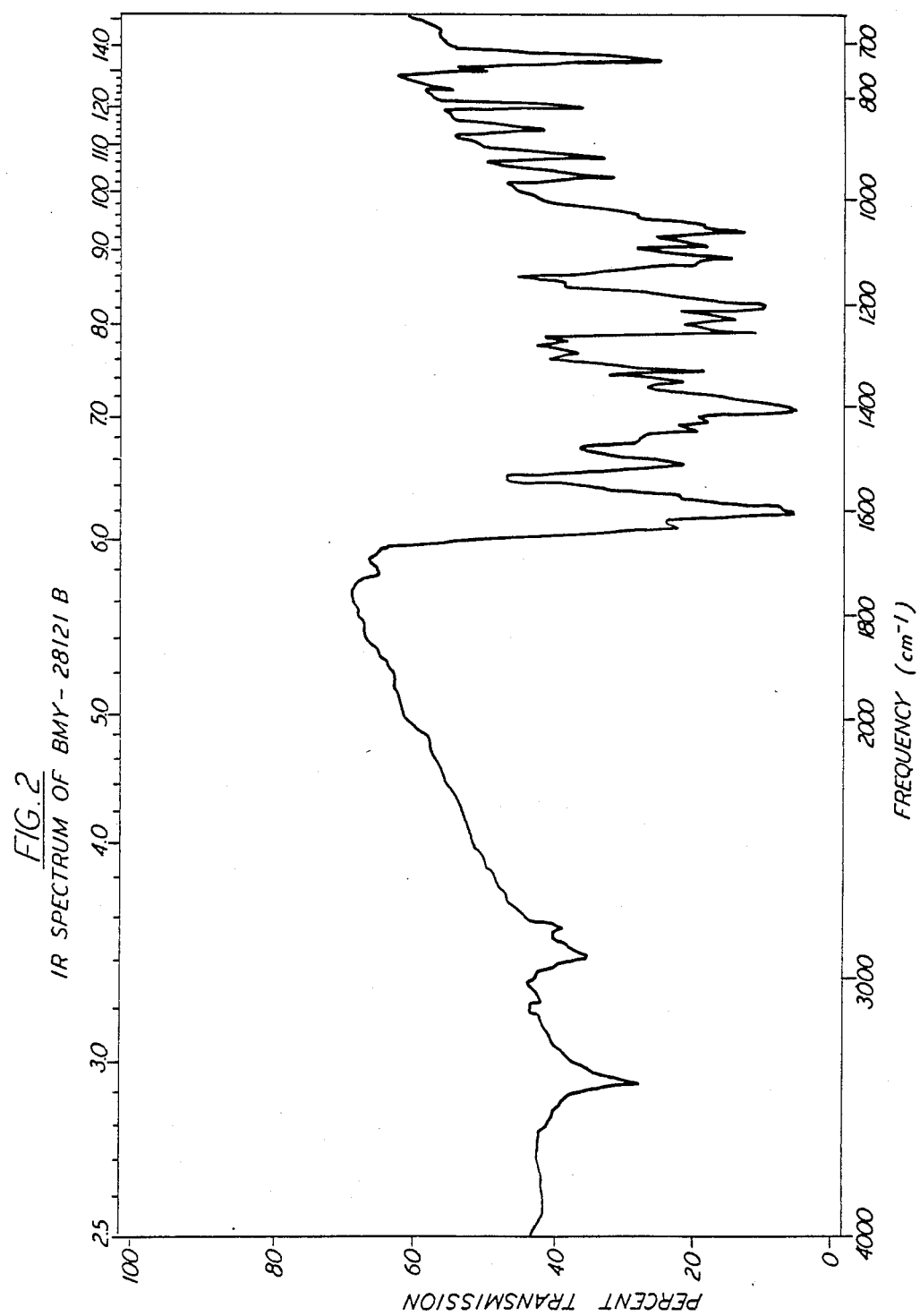
FIG. 2 shows the infrared absorption spectrum of BMY-28121B (KBr pellet).
Figure 3:
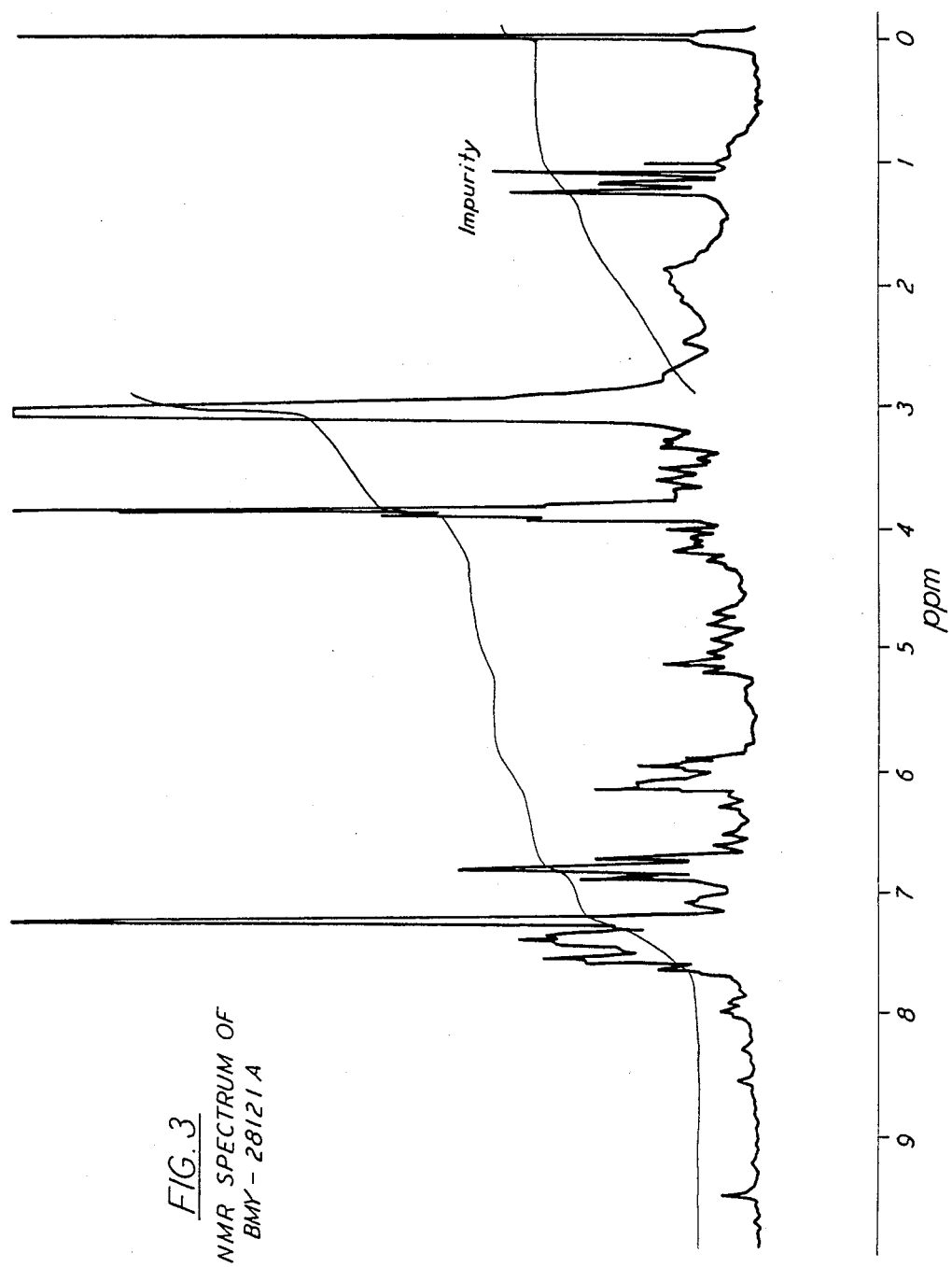
FIG. 3 shows the $^1$H NMR spectrum of BMY-28121A

BMY-28121A was isolated as a pale-yellow amorphous powder while BMY-28121B was isolated as yellow needles. Both forms of the antibiotic are readily soluble in methanol, ethanol, chloroform, pyridine, and dimethylformamide, slightly soluble in ethyl acetate and ethyl ether and practically insoluble in n-hexane and water. They give a positive response to Dragendorff, Rydon-Smith and Ehrlich reagents, but are negative to ninhydrin, ferric chloride and anthrone reagents. The molecular formulae of BMY-28121A and B were determined to be $C_{18}H_{21}N_3O_4$ and $C_{19}H_{23}N_3O_4$, respectively, based on the microanalyses and mass spectral results. Their physico-chemical data are summarized in Table 4. The UV spectra of both forms of BMY-28121 were similar, exhibiting the maxima at around 214, 235, and 335 nm in methanol. No shift was observed in acidic or alkaline solution. The IR spectra of BMY-28121 A and B are shown in FIGS. 1 and 2 and their ¹H-NMR spectra in FIGS. 3 and 4. The spectral data of BMY-28121 A and B are very similar, but a clear difference is observed in their ¹H-NMR. The spectrum of BMY-28121B shows two $OCH_3$ signals at δ: 3.36 and 3.90 ppm while BMY-28121A lacks the higher field $OCH_3$ signal (δ: 3.36 ppm). This difference was substantiated in their ¹³C-NMR spectra (Table 5). The spectrum of BMY-28121B indicates the presence of an $OCH_3$ carbon at α: 54.5 ppm which is absent in the spectrum of BMY-28121A. BMY-28121 A and B could not be differentiated by three TLC systems examined.

| Physico-chemical properties of BMY-28121 A and B | | | | |
|---|---|---|---|---|
| | BMY-28121 A | | BMY-28121 B | |
| Nature | Pale yellow powder | | Yellow needles | |
| M.P. (dec.) | 140–150° C. | | 164–166° C. | |
| $[\alpha]_D^{27}$ in $CHCl_3$ | +432° (c 0.46) | | +669° (c 0.62) | |
| Molecular formula | $C_{18}H_{21}N_3O_4$ | | $C_{19}H_{23}N_3O_4$ | |
| Anal | Calcd | Found | Calcd | Found |
| C % | 62.96 | 62.57 | 63.85 | 63.42 |
| H | 6.16 | 6.05 | 6.49 | 6.71 |
| N | 12.24 | 11.70 | 11.76 | 11.62 |
| MS m/z | 325 ($M^+$-$H_2O$) | | 325 ($M^+$-MeOH) | |
| UV $\lambda_{max}^{MeOH}$ nm(ε) | 281, 252 | | 281, 252 | |
| | 214 (22,000) | | 213 (27,800) | |
| | 235 (20,300) | | 236 (27,100) | |
| | 335 (45,500) | | 338 (57,500) | |
| TLC $SiO_2$, | | | | |
| EtOAc—Acetone(1:1) Rf | 0.14 | | 0.14 | |
| EtOAc—MeOH(9:1) | 0.20 | | 0.20 | |
| $CHCl_3$—MeOH(9:1) | 0.53 | | 0.53 | |

TABLE 5

¹³C-NMR of BMY-28121 A and B

| | Chemical shift in $CDCl_3$ δ in ppm, (multiplicity) | |
|---|---|---|
| Carbon | BMY-28121 A | BMY-28121 B |
| 1 | 34.4 (t) | 34.7 (t) |
| 2 | 126.4 (s) | 127.0 (s) |
| 3 | 135.9 (d) | 136.1 (d) |
| 5 | 163.9 (s) | 163.7 (s) |
| 5a | 121.0 (s) | 121.2 (s) |
| 6 | 117.1 (d) | 117.2 (d) |

TABLE 5-continued

| | $^{13}$C-NMR of BMY-28121 A and B | |
|---|---|---|
| | Chemical shift in CDCl$_3$ δ in ppm, (multiplicity) | |
| Carbon | BMY-28121 A | BMY-28121 B |
| 7 | 112.1 (d) | 111.9 (d) |
| 8 | 115.5 (d) | 115.6 (d) |
| 9 | 147.1 (s) | 146.9 (s) |
| 9a | 133.0 (s) | 133.5 (s) |
| 11 | 86.0 (d) | 87.8 (d) |
| 11a | 56.1 (d) | 56.1 (d) |
| 12 | 135.3 (d) | 135.2 (d) |
| 13 | 124.7 (d) | 124.6 (d) |
| 14 | 167.0 (s) | 166.8 (s) |
| N(CH$_3$)$_2$ | 36.1 (q) | 35.9 (q) |
| | 36.4 (q) | 37.3 (q) |
| C$_{11}$—OCH$_3$ | — | 54.5 (q) |
| C$_9$—OCH$_3$ | 59.3 (q) | 59.1 (q) |

Structure Determination

The structure study on BMY-28121 was carried out mostly on BMY-28121B. The physico-chemical properties and biological activity of the antibiotic suggested a resemblance to those of the anthramycin-sibiromycin group of antibiotics. Its strong UV absorption at around 335 nm indicated a close similarity to those of anthramycin and mazethramycin. However, unlike these antibiotics, BMY-28121B did not show bathochromic shift of the UV absorption in alkaline solution. A distinct difference to the known antibiotics of the anthramycin family was seen in the $^1$H-NMR spectrum which showed two N-CH$_3$ (δ: 3.04 and 3.10 ppm), two OCH$_3$ (δ: 3.36 and 3.90 ppm) and three aromatic protons (δ: 6.77, 6.89 and 7.63 ppm). The multiplicity of the aromatic protons (Table 6) was evidently assignable to 1,2,3 protons of a benzene nucleus. The $^1$N-NMR spectrum of BMY-28121B did not exhibit a phenolic hydroxyl proton, which together with the absence of UV bathochromic shift in alkaline solution, suggested an aromatic ring of unusual substitution for the anthramycin group antibiotics. This group of antibiotics have 1,2,4,5- or 1,2,3,4-tetrasubstituted or 1,2,3,4,5-penasubstituted benzene nucleus in the molecule. When refluxed with 1N NaOH for 35 minutes, BMY-28121 afforded two UV-absorbing compounds named as I and II. These fragments were purified by repeated chromatographic procedure to obtain homogeneous crystalline solids. The physico-chemical properties of compounds I and II are shown in Table 7. Compound I contains the 1,2,3-trisubstituted benzene moiety of the parent antibiotic as evidenced by the $^1$H-NMR spectrum. The spectrum also indicated the present of a OCH$_3$ group. Microanalysis and low field mass spectral results agreed with the molecular formula of C$_8$H$_9$NO$_3$. These data together with other physico-chemical data represented an aminomethoxy benzoic acid structure for compound I. J. F. Nyc and H. K. Mitchell reported a synthesis of 2-amino-3-methoxybenzoic acid, (J. Am. Chem. Soc. 70: 1847–1848, 1948) whose melting point and UV spectrum were found to be identical with those of compound I. Thus, compound I is determined to be 2-amino-3-methoxybenzoic acid.

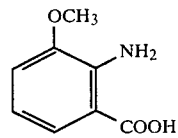

Compound I

Compound II was analyzed for C$_{10}$H$_{12}$N$_2$O$_2$ by mass spectral data (M$^+$: m/z=192) and microanalysis. The $^1$H-NMR spectrum of II indicated two N-CH$_3$ groups (δ: 3.08 ppm, s), two trans olefinic protons (δ: 6.63 ppm, d, J=15.2 Hz and 7.56 ppm, d, J=15.2 Hz), two aromatic protons (δ: 7.10 ppm, broad s and 7.27 ppm, broad s) and an aldehyde proton (δ: 9.50 ppm, s) and a NH-proton on aromatic ring (δ: 10.1 ppm, broad s). These resonance patterns suggested a resemblance to those of 4-allyl-2-formylpyrrole (J. Antibiotics 27: 866–873, 1974) which was obtained by alkaline hydrolysis of sibiromycin. Comparative spectral study of the two compounds revealed that compound II differed from 4-allyl-2-formylpyrrole in the replacement of an —CON(CH$_3$)$_2$ group by the —CH$_3$ group of the latter. Therefore, compound II was assigned to be 4-(2'-dimethylamidovinyl)-2-formylpyrrole.

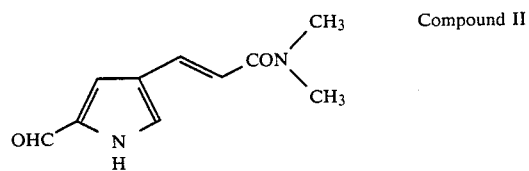

Compound II

Combination of above two fragments allowed us to propose the structure 1,10,11,11a-tetrahydro-9,11-dimethoxy-5H-pyrrolo[2,1-c][1,4]benzodiazepine-5-one-2-N,N-dimethylacrylamide for BMY-28121B. Stereochemistry on C$_{11}$ and C$_{11a}$ was established to be 11(R) and 11a(S) based on the fact that no splitting was observed between H$_{11}$ and H$_{11a}$ in the $^1$H-NMR spectrum (J. Antibiotics 36: 142–146, 1983). The IR, UV and MS spectral data of BMY-28121A quite resembled those of BMY-28121B. Their $^1$H-NMR spectra were also similar, the only difference being the lack of OCH$_3$ signal in BMY-28121A. This would account for the difference in molecular formulae and $^{13}$C-NMR data between BMY-28121 A and B. Thus, the structures of BMY-28121 A and B were determined as follows:

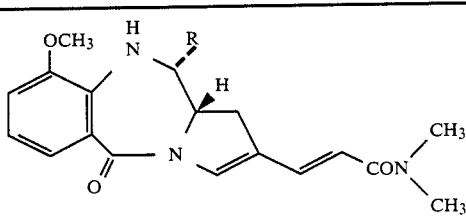

| | R |
|---|---|
| BMY-28121 A | OH |
| BMY-28121 B | OCH$_3$ |

TABLE 6

¹H—NMR of BMY-28121 B (CDCl₃, 360 MHz)

| Chemical shift δ (ppm) | Proton | Coupling multiplicity (J:Hz) | Assignment |
|---|---|---|---|
| 2.87 | 1H | dd (6.0 and 17.0) | H-1 |
| 3.04 | 3H | s | } —N—(CH₃)₂ |
| 3.10 | 3H | s | |
| 3.17 | 1H | dd (11.0 and 17.0) | H-1' |
| 3.36 | 3H | s | C-11 O—CH₃ |
| 3.90 | 3H | s | C-9 O—CH₃ |
| 4.27 | 1H | dd (6.0 and 11.0) | H-11a |
| 4.70 | 1H | d (6.0) | H-11 |
| 6.06 | 1H | d (15.2) | H-13 |
| 6.19 | 1H | d (6.0) | 10-NH |
| 6.77 | 1H | t (8.0) | H-7 |
| 6.89 | 1H | dd (2.5 and 8.0) | H-8 |
| 7.50 | 1H | d (15.2) | H-12 |
| 7.51 | 1H | s | H-3 |
| 7.63 | 1H | dd (2.5 and 8.0) | H-6 |

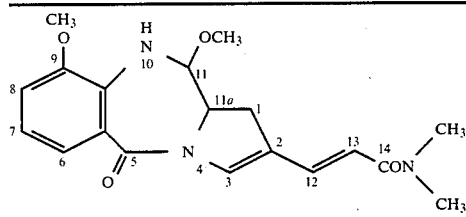

TABLE 7

Physico-chemical properties of compounds I and II

| | Compound I | Compound II |
|---|---|---|
| Nature | Colorless needles | Pale-yellow crystalline solid |
| M.P. | 175–6° C. | 155–7° C. |
| Molecular formula | C₈H₉NO₃ | C₁₀H₁₂N₂O₂ |

TABLE 7-continued

Physico-chemical properties of compounds I and II

| Anal | Calcd | Found | Calcd | Found |
|---|---|---|---|---|
| C % | 57.48 | 57.30 | 62.49 | 62.47 |
| H | 5.43 | 5.25 | 6.29 | 6.26 |
| N | 8.38 | 8.35 | 14.57 | 13.98 |
| MS m/z | 167 (M⁺), 149, 134 121, 106 | | 192 (M⁺), 148, 120 | |
| UV λ$_{max}^{MeOH}$ nm(ε) | 225 (27,200) 247 (sh, 7,200) 336 (5,600) | | 260 (16,400) 320 (15,500) | |
| IR ν$_{max}^{KBr}$ cm⁻¹ | 3500, 3380, 3000–2400 1670, 1590, 1555, 760 | | 3120, 1660, 1640, 1585 1560, 970 | |

Biological Activity

A. Antibacterial Activity

The minimum inhibitory concentration (MIC) of BMY-28121 A and B was determined for a variety of aerobic and anaerobic organisms by the serial two-fold dilution method. Nutrient agar (Eiken) was used for aerobic bacteria and GAM agar medium (Nissui) for anaerobic organisms. The inoculum size was adjusted to 10⁴ CFU/ml for aerobic bacteria and 10⁷–10⁸ for all anaerobic organisms. The antibacterial spectra of BMY-28121 A and B for aerobic bacteria were shown in Table 8 and for anaerobic organisms in Table 9.

All of the aerobic gram-positive bacteria tested, which included amino-glycoside or penicillin-resistant staphylococci, were moderately susceptible to BMY-28121 A and B. However, they did not show any in vitro activity against aerobic gram-negative organisms.

Against anaerobic bacteria, BMY-28121 A and B inhibited all of the gram-positive and negative organisms, which included the strains of clindamycin-resistant *C. difficile* and clindamycin or ampicillin-resistant *B. fragilis*. BMY-28121 B was about twice as active as BMY-28121 A against anaerobic organisms.

TABLE 8

In vitro activity against aerobic bacteria in nutrient agar

| | MIC (mcg/ml) | | | |
|---|---|---|---|---|
| Organism | BMY-28121A | BMY-28121B | Kanamycin | Ampicillin |
| *Staphylococcus aureus* 209P | 3.1 | 3.1 | 0.4 | <0.0063 |
| *Staphylococcus aureus* Smith | 3.1 | 1.6 | 0.4 | 0.05 |
| *Staphylococcus aureus* D136 | 6.3 | 6.3 | 0.8 | 0.8 |
| *Staphylococcus aureus* 52-34 | 3.1 | 3.1 | 0.8 | 1.6 |
| *Staphylococcus aureus* A20239 | 12.5 | 6.3 | 100 | 1.6 |
| *Staphylococcus aureus* BX-1633 | 12.5 | 6.3 | 0.8 | 3.1 |
| *Staphylococcus aureus* A15097 | 12.5 | 6.3 | 0.8 | 6.3 |
| *Staphylococcus epidermidis* D153 | 3.1 | 1.6 | 0.8 | 0.2 |
| *Staphylococcus epidermidis* A22152 | 6.3 | 3.1 | 25 | 0.4 |
| *Streptococcus faecalis* A9612 | 12.5 | 6.3 | 25 | 0.4 |
| *Micrococcus luteus* PCI-1001 | 12.5 | 12.5 | 6.3 | <0.0063 |
| *Bacillus subtilis* PCI-219 | 1.6 | 1.6 | 0.2 | 0.025 |
| *Escherichia coli* NIHJ | 50 | >50 | 1.6 | 0.2 |
| *Klebsielle pneumoniae* D-11 | >50 | >50 | 0.4 | 0.8 |
| *Proteus mirabilis* A9554 | >50 | >50 | 6.3 | 0.4 |
| *Proteus vulgaris* A9436 | >50 | >50 | 0.8 | 0.4 |
| *Morganella morganii* A9553 | >50 | >50 | 6.3 | >100 |
| *Serratia marcescens* A20222 | >50 | >50 | 3.1 | 12.5 |
| *Pseudomonas aeruginosa* A9930 | >50 | >50 | 6.3 | >100 |
| *Enterobacter cloacae* A9659 | >50 | >50 | 3.1 | 12.5 |

TABLE 9

In vitro activity against anaerobic bacteria in GAM agar

| | MIC (mcg/ml) | | | |
|---|---|---|---|---|
| Organism | BMY-28121A | BMY-28121B | Ampicillin | Clindamycin |
| *Clostridium difficile* A21675 | 6.3 | 3.1 | 1.6 | 50 |
| *Clostridium perfringens* A22787 | 0.8 | 0.4 | 0.1 | 0.05 |
| *Propionibacterium acnes* A21933 | 0.4 | 0.4 | 0.05 | 0.4 |

TABLE 9-continued

| | In vitro activity against anaerobic bacteria in GAM agar | | | |
|---|---|---|---|---|
| | MIC (mcg/ml) | | | |
| Organism | BMY-28121A | BMY-28121B | Ampicillin | Clindamycin |
| *Peptostreptococcus anaerobius* A21905 | 0.4 | 0.2 | 0.05 | 0.4 |
| *Bacteroides fragilis* A22693 | 1.6 | 1.6 | 3.1 | 0.1 |
| *Bacteroides fragilis* A22053 | 0.8 | 0.4 | 3.1 | 0.2 |
| *Bacteroides fragilis* A22021 | 0.8 | 0.2 | 3.1 | 0.1 |
| *Bacteroides fragilis* A21916 | 1.6 | 0.8 | 12.5 | 0.05 |
| *Bacteroides fragilis* A22534 | 1.6 | 0.4 | >100 | 1.6 |
| *Bacteroides fragilis* A22695 | 1.6 | 0.4 | >100 | 0.1 |
| *Bacteroides fragilis* A22533 | 1.6 | 0.8 | >100 | 0.1 |
| *Bacteroides fragilis* CUH-108 | 0.8 | 0.4 | 50 | 100 |

B. Antitumor Activity

Antitumor activity of BMY-28121 A and B was determined in mice (male $BDF_1$ strain). Lymphocytic leukemia P388 and lymphoid leukemia $L_{1210}$ were implanted by intraperitoneal injection of 0.4 ml diluted ascitic fluid containing $10^6$ and $10^5$ cells, respectively. Melanotic melanoma B16 was implanted 0.5 ml of a 10% tumor brei. The antibiotics were dissolved in 0.9% saline containing 10% dimethyl sulfoxide and graded doses of them were administered to mice intraperitoneally 24 hours after tumor inoculation. The treatments were given once daily for 9 days. Mitomycin C was comparatively tested as a reference compound in the experiments.

The results are shown in Table 10. BMY-28121 A and B were approximately 4 times more active than mitomycin C against P388 leukemia in terms of minimum effective dose. BMY-28121 B showed potent therapeutic activity against L1210 leukemia, however it was marginally active against B16 melanoma.

The acute toxicity of BMY-28121 B was determined in mice (male ddY strain) by single intraperitoneal administration, the $LD_{50}$ being 0.81 mg/kg.

TABLE 10

| Antitumor activity of BMY-28121 A and B | | | | | | | | |
|---|---|---|---|---|---|---|---|---|
| T/C % of MST* | | | | | | | | |
| Dose in mg/kg/day, ip | | | | | | | | |
| | 1 | 0.5 | 0.25 | 0.13 | 0.063 | 0.031 | 0.016 | 0.008 |
| P388 leukemia | | | | | | | | |
| BMY-28121 A | | 100 | (231**) | (231) | (180) | (140) | (130) | 110 |
| BMY-28121 B | | | (215) | (200) | (170) | (160) | (140) | 120 |
| Mitomycin C | (450) | (240) | (180) | (150) | (140) | 120 | | |
| L1210 leukemia | | | | | | | | |
| BMY-28121 B | | | (129) | (129) | (129) | 106 | 94 | |
| Mitomycin C | (141) | (141) | (129) | (129) | 106 | | | |
| B16 melanoma | | | | | | | | |
| BMY-28121 B | | | (131) | 113 | 106 | 100 | | |
| Mitomycin C | (191) | (164) | (136) | 124 | | | | |

*Ratio of median survival time of test and control animals
**Circled values indicate significant antitumor effect As shown above BMY-28121 A and B possess antibacterial activity against various gram-positive and anaerobic bacteria and are thus useful in the therapeutic treatment of mammals and other animals for infectious diseases caused by such bacteria. Additionally, they may be used for other conventional applications of antibacterial agents such as disinfecting medical and dental equipment.

The marked antitumor activity shown against experimental tumors in mice, eg. P388 leukemia, indicates that BMY-28121 A and B are also therapeutically useful in inhibiting the growth of mammalian tumors.

The present invention, therefore, provides a method for therapeutically treating an animal host affected by a bacterial infection or by a malignant tumor which comprises administering to said host an effective antibacterial or tumor-inhibiting dose of BMY-28121 A or B or a pharmaceutical composition thereof.

In another aspect the present invention provides a pharmaceutical composition which comprises an effective antibacterial or tumor-inhibiting amount of BMY-28121 A or B, or a mixture thereof, in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the BMY-28121 antibiotic used will vary according to the particular composition formulated, the mode of application and the particular situs, host and disease being treated. Many factors that modify the action of the drug will be taken into account by those skilled in the art, for example, age, body, weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage administration tests in view of the above guidelines.

The following examples are provided for illustrative purposes only and are not intended to limit the scope of the invention. DIAION HP-20 (Trademark of Mitsubishi Chemical Industries, Japan) is a nonionic macroreticular (macroporous) polymer resin. Unless otherwise indicated, solvent ratios used below are volume-volume.

EXAMPLE 1

Fermentation of BMY-28121

A well grown agar slant of *Streptomyces albus,* K731-113, was used to inoculate a vegetative medium consisting of 2% soluble starch, 1% beet molasses, 1% fish meal and 0.5% CaCO$_3$, the pH being adjusted to 7.0 before sterilization. The vegetative medium was incubated at 28° C. for 3 days on a rotary shaker (250 rpm) and 5 ml of the growth was transferred into a 500 -ml Erlenmeyer flask containing 100 ml of the fermentation medium having the same composition as the vegetative medium. The fermentation was carried out at 28° C. for 7 to 8 days on a rotary shaker. The antibiotic activity in the fermentation broth was determined by paper disc agar diffusion method using *Bacillus subtilis* M45 (Rec$^-$mutant) and *Bacteroides fragilis* as the test organism. After seven days cultivation, the antibiotic activity obtained a maximum potency of 60–100 mcg/ml. The fermentation was also carried out in a stir-jar fermenter. A 500-ml portion of the seed culture was transferred into 10 liters of the fermentation medium in a 20-liter fermenter. The stir-jar fermentation was carried out at 28° C. with agitation at 250 rpm and aeration of 10 liters per minute. The antibiotic production showed a maximum potency of 100 mcg/ml after 70–90 hours fermentation.

The antitumor activity of the fermentation broth was extracted and purified by the following two processes to isolate BMY-28121 A and B individually.

Isolation of BMY-28121 A

Ten liters of the fermentation broth was separated into the mycelial cake and the filtrate by aid of a Sharpless centrifuge. The cake was stirred with 1.3 liters of acetone to extract the activity. The acetone extract was combined with the broth filtrate and the solution stirred with DIAION HP-20 (900 ml) for 30 minutes. The resin was then separated, washed with water (2 L) and eluted twice with 90% aqueous acetone (2 L each). The eluates were concentrated in vacuo to an aqueous solution which was extracted with 800 ml of n-butanol. Evaporation of the n-butanol extract afforded 1.88 grams of crude BMY-28121A.

The solid was dissolved in 25 ml of 50% aqueous acetone and applied on a column of DIAION HP-20 (230 ml) which had been equilibrated with 50% aqueous acetone solution. The elution was carried out with the same solution and the eluate monitored by bioassay against *B. subtilis* M45 (Rec$^-$mutant). The active fractions were pooled, evaporated in vacuo and lyophilized to give a pale-yellow solid of semi-pure antibiotic (504 mg). The solid was chromatographed on silica gel (150 ml) developing with a chloroform-acetone mixture (2:1). Evaporation of the major bioactive fractions afforded 197 mg of BMY-28121A which appeared as a single spot on TLC.

Isolation of BMY-28121B

The fermentation broth (15 L) was separated into the mycelial cake and the supernatant as described above. The activity in the mycelial cake was recovered by shaking twice with 1 liter each of methanol. The broth supernatant was stirred with DIAION HP-20 (1 L) for one hour. The resin was separated, washed with water and then stirred with 5.5 L of 90% aqueous acetone to elute the activity. The eluates were combined with the methanol extracts of mycelial cake and concentrated in vacuo to an aqueous solution which was extracted with two 1.0 L-portions of n-butanol. Evaporation of the extracts afforded 2.21 g of crude solid of BMY-28121B. The solid was dissolved in 40 ml of 40% aqueous methanol and charged on a column of DIAION HP-20 (220 ml) which was developed with 80% aqueous methanol. Upon assay against *B. subtilis* M45, the appropriate eluates were pooled and concentrated in vacuo to give light-brown powder (333 mg). This solid was chromatographed on a silica gel column (Wakogel C-200, 70 g) using a mixture of chloroform-methanol (20:1) as the developing solvent. The bioactive fractions were pooled and evaporated to a residue (213 mg) which was crystallized from a mixture of ethyl acetate-methanol (20:1) to deposit yellow needles of BMY-28121B (90 mg).

We claim:

1. The antibiotic BMY-28121A of the formula

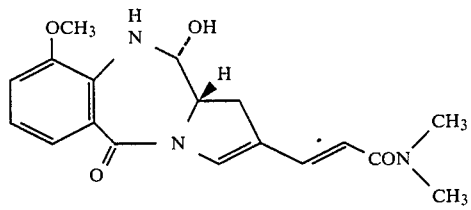

2. The antibiotic BMY-28121B of the formula

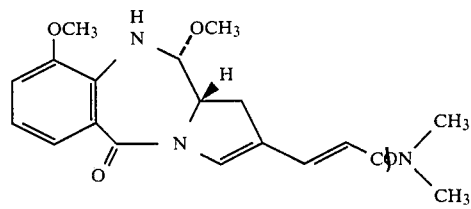

3. A method for therapeutically treating an animal host affected by a bacterial infection, which comprises administering to said host an effective antibacterial dose of BMY-28121A.

4. A method for therapeutically treating an animal host affected by a bacterial infection, which comprises administering to said host an effective antibacterial dose of BMY-28121B.

5. A method for therapeutically treating an animal host affected by a malignant tumor sensitive to BMY-28121A, which comprises administering to said host a tumor-inhibiting dose of BMY-28121A.

6. A method for therapeutically treating an animal host affected by a malignant tumor sensitive to BMY-28121B, which comprises administering to said host a tumor-inhibiting dose of BMY-28121B.

7. A pharmaceutical composition for treatment of bacterial infections comprising an effective antibacterial amount of BMY-28121A in combination with a pharmaceutical carrier or diluent.

8. A pharmaceutical composition for treatment of bacterial infections comprising an effective antibacterial amount of BMY-28121B in combination with a pharmaceutical carrier or diluent.

9. A pharmaceutical composition for treatment of malignant tumors in mammalian hosts comprising an effective tumor-inhibiting amount of BMY-28121A in combination with a pharmaceutical carrier or diluent.

10. A pharmaceutical composition for treatment of malignant tumors in mammalian hosts comprising an effective tumor-inhibiting amount of BMY-28121B in combination with a pharmaceutical carrier or diluent.

* * * * *